(12) United States Patent
Fornoni et al.

(10) Patent No.: US 10,980,828 B2
(45) Date of Patent: *Apr. 20, 2021

(54) METHOD OF USING CYCLODEXTRIN (71) Applicant: L&F Research LLC, Miami, FL (US)

(72) Inventors: Alessia Fornoni, Miami, FL (US); Sandra Merscher-Gomez, Miami, FL (US)

(73) Assignee: L & F Research LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/227,018

(22) Filed: Dec. 20, 2018

(65) Prior Publication Data

US 2019/0262385 A1    Aug. 29, 2019

Related U.S. Application Data

(63) Continuation of application No. 14/391,236, filed as application No. PCT/US2013/036484 on Apr. 12, 2013, now Pat. No. 10,195,227.

(60) Provisional application No. 61/624,087, filed on Apr. 13, 2012.

(51) Int. Cl.
| | | |
|---|---|---|
| *A61K 31/724* | (2006.01) | |
| *A61K 31/155* | (2006.01) | |
| *A61K 31/455* | (2006.01) | |
| *A61K 38/00* | (2006.01) | |
| *A61K 38/28* | (2006.01) | |
| *A61K 45/06* | (2006.01) | |

(52) U.S. Cl.
CPC .......... *A61K 31/724* (2013.01); *A61K 31/155* (2013.01); *A61K 31/455* (2013.01); *A61K 38/00* (2013.01); *A61K 38/28* (2013.01); *A61K 45/06* (2013.01)

(58) Field of Classification Search
CPC .................................................. A61K 31/724
See application file for complete search history.

(56) References Cited

U.S. PATENT DOCUMENTS

| | | | |
|---|---|---|---|
| 5,132,298 | A | 7/1992 | Ueno |
| 6,890,549 | B2 | 5/2005 | Artiss et al. |
| 7,276,351 | B2 | 10/2007 | Teich et al. |
| 8,101,201 | B2 | 1/2012 | Artisa |
| 8,202,702 | B2 | 6/2012 | Neilson et al. |
| 8,263,413 | B1 | 9/2012 | Hansen |
| 8,455,471 | B2 | 6/2013 | Wisdom et al. |
| 8,586,076 | B2 | 11/2013 | Artiss et al. |
| 8,975,241 | B2 | 3/2015 | Han et al. |
| 9,326,539 | B2 | 5/2016 | Artiss et al. |
| 2003/0133904 | A1 | 7/2003 | Dagan et al. |
| 2004/0121983 | A1 | 6/2004 | Chattopadhyay et al. |
| 2005/0287205 | A1* | 12/2005 | Wang .......... A61K 31/19 424/451 |
| 2006/0128653 | A1 | 6/2006 | Tang et al. |
| 2006/0148721 | A1 | 7/2006 | Erondu |
| 2006/0172939 | A1 | 8/2006 | Bellotti |
| 2007/0197438 | A1 | 8/2007 | Reiser et al. |
| 2007/0292837 | A1 | 12/2007 | Deutsch et al. |
| 2009/0324624 | A1 | 12/2009 | Shibata |
| 2010/0184809 | A1 | 7/2010 | Kremoser |
| 2010/0189653 | A1 | 7/2010 | Robbins et al. |
| 2011/0257240 | A1 | 10/2011 | Pavliv |
| 2011/0314423 | A1 | 12/2011 | Belotti et al. |
| 2012/0196831 | A1 | 8/2012 | Han |
| 2012/0251527 | A1 | 10/2012 | Reiser |

FOREIGN PATENT DOCUMENTS

| | | |
|---|---|---|
| EP | 1125584 A1 | 8/2001 |
| JP | 2004323443 A | 11/2004 |
| JP | 2008523096 A | 7/2008 |
| JP | 2008528610 A | 7/2008 |
| JP | 2009298820 A | 12/2009 |
| JP | 2010506942 A | 3/2010 |
| JP | 2010508372 A | 3/2010 |
| JP | 2012505251 A | 3/2012 |
| WO | 199710828 A1 | 3/1997 |
| WO | 2006071491 A1 | 7/2006 |
| WO | 2006081363 A1 | 8/2006 |
| WO | 2008055871 A1 | 5/2008 |
| WO | 2009142988 A2 | 11/2009 |
| WO | 2010042202 A1 | 4/2010 |
| WO | 2010042886 A2 | 4/2010 |
| WO | 2010054167 A2 | 5/2010 |
| WO | 11043630 A2 | 4/2011 |
| WO | 2011043630 A2 | 4/2011 |
| WO | 2012012473 A1 | 1/2012 |
| WO | 2012/054321 A2 | 4/2012 |
| WO | 2012054321 A2 | 4/2012 |

OTHER PUBLICATIONS

Office Action/Examination report in corresponding Canadian Application No. 2870316 dated Apr. 5, 2019 (pp. 1-6).
Extended European Search Report dated Jun. 29 2016, issued in corresponding European Application No. 13775223, 11 pages.
Wijesekara, N. et al., "miR-33a Modulates ABCA1 Expression, Cholesterol Accumulation, and Insulin Secretion in Pancreatic Islets", Diabetes, XP055248061, vol. 61, No. 3, Feb. 7, 2012, pp. 653-658.
International Preliminary Report on Patentability and Written Opinion for PCT/US2013/036484 (issued by the International Bureau Oct. 23, 2014).
Camargo et al., "Cyclodextrins in the treatment of mouse model of Niemann-Pick disease", Life Sciences 70 (2): pp. 131-142 (2001)—Abstract only.
International Search Report dated Nov. 5, 2013 in WO 2013/155485 (Fornoni et al.) published Oct. 17, 2013, all pages.

(Continued)

*Primary Examiner* — Leigh C Maier
(74) *Attorney, Agent, or Firm* — Millen, White, Zelano & Branigan, PC; Ted W. Whitlock (57) ABSTRACT

Described are methods for using cyclodextrin to treat, inhibit, prevent, ameliorate, or cure diabetes or conditions relating to diabetes.

11 Claims, 6 Drawing Sheets

Specification includes a Sequence Listing.

(56) References Cited

OTHER PUBLICATIONS

Reiser et al., "Toward the development of podocyte-specific drugs", Kidney International, vol. 77, pp. 662-668, published online Feb. 3, 2010.
Saleem et al., "A conditionally immortalized human podocyte cell line demonstrating nephrin and podocin expression", Journal of the American Society of Nephrology, vol. 13, pp. 630-638, 2002.
Munkert et al., "Characterization of the transcriptional regulation of the human MT1-MMP gene and association to risk reduction for focal-segmental glomerulosclerosis with two functional promoter SNPs", Nephrology Dialysis Transplantation, vol. 24, pp. 735-742, 2009, published online Oct. 16, 2008.
Harendza et al., "The transcriptional regulation of podocin (NPHS2) by Lmx1b and a promoter single nucleotide polymorphism", Cellular & Molecular Biology Letters, vol. 14, pp. 679-691, Jun. 27, 2009.
Perosa et al., "Generation of biologically active linear and cyclic peptides has revealed a unique fine specificity of rituximab and its possible cross-reactivity with acid sphingomyelinase-like pohophodiesterase 3b precursor", Blood, vol. 107, No. 3, pp. 1070-1077, Feb. 2006.
Moeller et al., "Two gene fragments that direct podocyte-specific expression in transgenic mice", Journal of the American Society of Nephrology, vol. 13, pp. 1561-1567, 2002.
Delville et al., "B7-1 blockade does not improve post-transplant nephrotic syndrome caused by recurrent FSGS", Journal of the American Society of Nephrology, doi: 10, 1681/ASN.2015091002, pp. 1/8-8/8, 2015.
GenBank Accession No. NM_001009568, 1, GI: 57242799, publicly available Jul. 2010.
GenBank Accession No. NM_014474.2, GI: 57242797, publicly available Jul. 1010.
Coward et al., "Nephrotic plasma alters slit diaphragm-dependent signaling and translocates nephrin, podocin, and CD2 associated protein in cultured human podocytes", Journal of the American Society of Nephrology: JASN, vol. 16, No. 3, pp. 629-637, Jan. 19, 2005.
Alam et al., Chapter 6, "Reporter gene for monitoring expression in mammalian cells, S.C. Makrides (Ed.) in Gene Transfer and Expression in Mammalian Cells", Elsevier Science B.V., pp. 291-308, 2003.
Cormack-Aboud et al., "Rosuvastatin protects against podocyte apoptosis in vitro", Nephrology, Dialysis, Transplantation, vol. 24, pp. 404-412, 2009 (advanced access publication Sep. 27, 2008).
Society News: 2009 Archives. American Society of Nephrology, Society News—2009 Archives, printed from http://www.asn-online.org/news/2009/ as p. 1/1 on Jun. 3, 2015.
Bijian et al., "Actin cytoskeletoon regulates extracellular matrix-dependent survival signals in glomerular epithelial cells", American Journal of Physiology, vol. 289, pp. F1313-F1323, 2005.
Sun et al., "Glomerular transcriptome changes associated with lipopolysaccharide-induced proteinuria", American Journal of Nephrology, vol. 29, pp. 558-570, Jan. 9, 2009.
Reiser et al., "Regulation of mouse podocyte process dynamics by protein tyrosine phosphatases", Kidney International, vol. 57, pp. 2035-2042, 2000.
Srivastava et al., LPS and PAN-induced podocyte injury in an in vitro model of minimal change disease: changes in TLR profile, Journal of Cell Communications and Signaling, vol. 7, pp. 49-60, Nov. 2013.
Ahern. Biochemical, reagents kits offer scientists god return on investment, The Scientist, vol. 9 No. 15, p. 20, Jul. 1985, printed as pp. 1/7-7/7.
Hattori et al., "Increase of integrin-linked kinase activity in cultured podocytes upon stimulatioin with plasma from patients with recurrent FSGS", American Journal of Transplantation, vol. 8, pp. 1550-1556, 2008.
Chen et al., "Visualize circulating factor by using podocytes as target cell in patients with FSGS", Presented at the Ameerican Society of Nephrology meeting (Oct. 30, 2009) San Diego, CA (abstract only).
Collino et al., "Preeclamptic sera induce nephrin shedding from podocytes through endothelin-1 release by endothelial golmerular cells", Am J. Physical Renal Physical (Feb. 2008), vol. 294, pp. F1185-F1194.
Doublier et al., "Nephrin redistribution on podocytes is a potential mechanism for proteinuria in patients with primary acquired nephrotic syndrome", Am J Pathology (May 2001), vol. 156, pp. 1723-1731.
Fornoni et al., "Efffect of Ritusimab on the regulation of sphingomyelinase-like phosphodiesterase 3b-precursor in recurrent FSGS", ASN Renal Week, San Diego (Nov. 2009): Abstract No. 552231 (3 pages).
Fornoni et al., "Rituximab affects podocytes in recurrent FSGS via sphingomyelination", Poster International Podocyte Meeting (Jun. 2010) Bristol, UK (1 page).
Letavernier et al, "mToR inhibitors-induced proteinuria: Mechanisms, significance, and management", Transplanation Reviews, (2008), vol. 22, pp. 125-130.
Sageshima et al., "Rituximab may decrease the incidence of FSGS recurrence after kidney transplantation (KT) by preventing down regulation of sphingomyelinase-like phosphodiesterase 3b-precursor (SMLPD-3b) in the podocyte", American Transplant Society meeting, San Diego, (May 2010): Abstract No. 252551 (2 pages).
Fornoni et al., "Rituximab targets podocytes in recurrent focal segmental glomerulosclerosis", Sci. Trans!. Med. (Jun. 1, 2011), vol. 3, 85ra46, pp. 1-10.
Tufro A, "Cholesterol accumulation in podocytes: a potential novel targetable pathway in diabetic nephropathy", Diabetes. Nov. 2013; 62(11):3661-2.
Merscher-Gomez S, "Cyclodextrin protects podocytes in diabetic kidney disease", Diabetes. Nov. 2013; 62 (11):3817-27.
Chapman, J. M., "Pitavastatin: novel effects on lipid parameters" Atheroscler Suppl. Nov. 2011;12(3):277-84.
Hideki, Ozasa. et al., "Pioglitazone enhances cholesterol efflux from macrophages by increasing ABCA1/ABCG1 expressions via PPARy/LXRα pathway: findings from in vitro and ex vivo studies" Atherosclerosis, Elsevier Ireland LTD, IE, vol. 219, No. 1, Jul. 25, 2011, pp. 141-150, ISSN: 0021-9150.
Kilsdonk E. P. C. et al., "Cellular Cholesterol Efflux Mediated by Cyclodextrins", Journal of Biological Chemistry, American Society for Biochemistry and Molecular Biology, XP001146317, vol. 270, No. 29, Jul. 21, 1995, pp. 17250-17256.
Tang, C. et al., "Diabetes reduces the cholesterol exporter ABCA1 in mouse macrophages and kidneys", Journal of Lipid Research, XP055268069, vol. 51, No. 7, Jul. 1, 2010, pp. 1719-1728.
Search Report dated Jan. 10, 2017, issued in corresponding Canadian Application No. 2852904 (7 pages).
Fornoni et al., Abstract TH-FC048, Renal Week 2009, American Society of Nephrology, San Diego, CA, USA; available online at the "Renal Week 2009 Abstract Supplement (PDF)" , p. 12A (under "Archives 2009-2003"): downloaded from http://www.asn-online.org/abstracts/ on Jan. 26, 2017.
Shi SF, Wang SX, Zhang YK, et al. Ultrastructural features and expression of cytoskeleton proteins of podocyte from patients with minimal change disease and focal segmental glomerulosclerosis, Ren Fail , 2008, vol. 30 (p. 477-483).
Barisoni L. et al., J Am Soc Nephroi., vol. 10, pp. 51-61, Jan. 1999 (Jan. 1999).
Faul C. et al., Nat Med., vol. 14, pp. 931-938, Sep. 2008 (Sep. 2008).
Office Action from corresponding copending U.S. Appl. No. 13/879,892 dated Dec. 27, 2017.
Hristea et al., "Successful treatment of recurrent focal segmental glomerulosclerosis after kidney transplantation by plasmapheresis and rituximab" Transplant International.Jan. 2007 ; vol. 20, Issue 1, pp. 102-105.
Park et al. "Investigation of toxic metabolites during drug development." Toxicol Appl Pharmacol. Sep. 1, 2005;207(2 Suppl):425-34.
International Preliminary Report on Patentability and Written Opinion for PCT/US2013/036484 (issued by the International Bureau dated Oct. 23, 2014).

(56) References Cited

OTHER PUBLICATIONS

Camargo et al., "Cyclodextrins in the treatment of mouse model of Niemann-Pick disease", Life Sciences 70 (2): pp. 131-142 (2001).
International Search Report dated Nov. 5, 2013 in WO 2013155485 (Fornoni et al.) published Oct. 17, 2013, all pages.
Society News: 2009 Archives. American Society of Nephrology, Society News—2009 Archives, printed from http://www.asn-online.org/news/2009/ as p. 1/1 on Oct. 17, 2016.
Ahern. Biochemical, reagents kits offer scientists god return on investment, The Scientist, vol. 9 No. 15, pp. 20, Jul. 1995, printed as pp. 1/7-7/7.
Hattori et al., "Increase of integrin-linked kinase activity in cultured podocytes upon stimulation with plasma from patients with recurrent FSGS", American Journal of Transplantation, vol. 8, pp. 1550-1556, 2008.
Fornoni et al., "Rituximab targets podocytes in recurrent focal segmental glomerulosclerosis", Sci. Transl. Med. (Jun. 1, 2011), vol. 3, 85ra46, pp. 1-10.
Spino et al., "Changing the Paradigm for the Treatment and Development of New Therapies for FSGS"Front Pediatr. Mar. 2016; 4:25.
Pullen et al.,"Drug discovery in focal and segmental glomerulosclerosis." Kidney Int. Jun. 2016;89(6):1211-20. (Epub Apr. 23, 2016).
Office Action in corresponding CN application 201380019867.5 dated Sep. 28, 2018 {pp. 1-5) and translated english summary of relevant portion.
Office Action in corresponding MX/a/2014/0122200 dated Aug. 16, 2018 (pp. 1-5) and translated English summary of same.
Zhang, Y. et al "Activation of the nuclear receptor FXR . . . " PNAS, vol. 103, No. 4, pp. 1006-1011. (Year: 2006).
Office Action in corresponding European application No. 13 775 223.4 dated Jul. 31, 2018.
Office Action in corresponding U.S. Appl. No. 14/967,831 dated Jun. 13, 2018.
English translation of Office Action in corresponding CN application No. 2013-80019867.5 dated May 8, 2018.
English translation of Office Action in corresponding JP application No. 2015-505963 dated Apr. 10, 2018.
Frijlink: Pharmaceutical Research, 1991,8 {1), p. 9-16.
Office Action in corresponding MX application No. 2014-012200 dated Mar. 1, 2018 and translation thereof.
Christian A., Use of cyclodextrins for manipulating cellular cholesterol content, J Lipid Res. Nov. 1997;38 11):2264-72.
Tae-Hyun Yoo : "Sphingomyelinase-Like Phosphodiesterase 3b Expression Levels Determine Podocyte Injury Phenotypes in Glomerular Disease" Journal of the American Society of Nephrology, vol. 26, pp. 133-147, 2015, pub Jun. 12, 2014. {Year: 2014).
Timarchi, H. Abatacept and glomerular diseases: The open road for the second signal as a new target is settled own. Recent Patents on Endocrine, Metabolic & Immune Drug Discovery, vol. 9,pp. 2-14, 2015. (Year: 2015).
PTO Form 892 from corresponding copending U.S. Appl. No. 13/879,892 dated Dec. 27, 2017.
Office Action/Examination report in corresponding MexicanApplication No. MX/a/2014/012200 dated Apr. 17, 2019 (pp. 1-6).
Office Action in corresponding CN Application No. 201380019867.5 dated Nov. 1, 2017.
Yun, J. et al "Possible anti-obesity therapeutics . . . " Phytochem., val 71, pp. 1625-1641. (Year: 2010).
Jiang, T. et al "Farnesoid X receptor modulates renal lipid . . . " Diabetes, val 56, pp. 2485-2493. (Year: 2007).
Kambham, N. et al "Obesity-related glomerulopathy . . . "Kidney Int., val 59, pp. 1498-1509. (Year: 2001).
Morales, E et al "Beneficial effects of weight loss . . . " Kidney Dis., vol. 41, pp. 319-327. (Year: 2003).
Notice of Rejection in corresponding Japan application No. 2015-505963 dated Aug. 8, 2017.
Yancey, P. et al., The Journal of Biological Chemistry, vol. 271, No. 27, pp. 16026-16034, published on Jul. 5, 1996.
Englsih language translation of Office Action in corresponding Chinese Application No. 2013800198675 dated Apr. 20, 2017.
Machine translation of JP2004323443A published Nov. 18, 2004 to Tokai Univ.
Office Action in corresponding JP Appln. No. 2015-505963 dated Jan. 31, 2017.
Office Action in corresponding JP Application No. MX/a/2014/012200 dated Sep. 5, 2017.
The Merck Manual, 1992, pp. 1700-1702.
Delville et al., J. Am. Soc. Nephrol., 2016, vol. 27, pp. 2520-2527.
Adelman et al., J. Pediatr., 2001, vol. 138, pp. 481-485.
Gohh et al., Am. J. Transplantation, 2005, vol. 5, pp. 2907-2912.
Haynes, A. et al "Anorecctic, thermogenic and anti-obesity activity . . . " Regulatory Peptides (2002) vol. 104, pp. 153-159.
English-language translation of Chinese Office Action, dated Feb. 5, 2016.
Atger, V. M. et al." Cyclodextrins as catalysts for the removal of cholesterol from macrophage foam cells." J. Clin. Invest. 99, 773 780 (1997).
Office Action in corresponding CA 2,870,316 dated Apr. 20, 2020 (pp. 1-5).
Office Action/Examination report in corresponding EP Application No. 13 775 223.4 dated Jan. 8, 2020 (pp. 1-4).
Second Office Action dated Apr. 28, 2020, in corresponding Japanese patent application No. 2018-150978 (pp. 1-4 and english translation pp. 1-4).
Office Action in corresponding CA 2,870,316 dated Jan. 20, 2021 (pp. 1-5).

* cited by examiner

|  | Het | Het+CD | Homo | Homo+CD |
|---|---|---|---|---|
| Hb (g/dl) | 15.9±0.9 | 16.5±0.6 | 14.5±3.7 | 15.1±1.2 |
| AST (U/l) | 146±25 | 111±44 | 143±78 | 157±26 |
| ALT (U/l) | 12±7 | 14±9 | 22±13 | 37±22 |
| GGT (U/l) | 5.2±2.5 | 4.6±0.3 | 6.5±3.5 | 5.2±2.3 |
| Cholesterol (mg/dl) | 46±7 | 105±9[###] | 95±4*** | 197±17[###] |

FIG. 3

SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aacagtttgt ggccttttg                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agttccaggc tggggtactt                                                   20

<210> SEQ ID NO 3
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 3
tcactccatc tcaagcatcg                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtggtcctc tcacaccagt                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggcatttgac agcactagca                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gctggaatga cagcttcaca                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtcagtggtg gacctgacct                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggacatgcac aaggtcctga                                                 20

<210> SEQ ID NO 9
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 9
cagaaaatcc tggagcttca aa                                              22
```

METHOD OF USING CYCLODEXTRIN

CROSS-REFERENCE TO RELATED APPLICATIONS

This application is a national stage filing under 35 U.S.C. 371 claiming priority to international application, PCT/US2013/036484, filed Apr. 12, 2013, which claims priority to or the benefit of U.S. provisional patent application, Ser. No. 61/624,087, filed Apr. 13, 2012, which are incorporated herein by reference in their entireties.

The instant application contains a sequence listing which has been submitted electronically in ASCII format and is hereby incorporated by reference in its entirety. Said ASCII copy, created on Apr. 3, 2019, is named LFR-0002-C01_SL.txt and is 2,359 bytes in size.

BACKGROUND OF THE INVENTION

This invention generally relates to a method for lowering plasma membrane and cellular cholesterol for the prevention, treatment, cure, or reversal of obesity, metabolic syndrome, diabetes, or a complication relating thereto, by administering to a patient in need thereof, a compound, such as a cyclodextrin or derivative thereof, to lower plasma membrane and cellular cholesterol and/or lipid.

Obesity, metabolic syndrome, pre-diabetes and diabetes represent a worldwide epidemic with a major health care cost, as all these prevalent medical conditions are major risk factors for cardiovascular morbidity and mortality.

It is well established that elevated plasma cholesterol levels and, in particular, low-density lipoprotein (LDL) cholesterol levels, play an important role in the development of coronary heart disease, stroke, peripheral vascular disease, kidney disease, atherosclerosis and hypertension. Clinical trials have demonstrated that decreasing cholesterol concentrations in the plasma has a major impact on cardiovascular morbidity and mortality. Therefore, therapeutic control of systemic hypercholesterolemia is critically important in the clinical management and treatment of obesity, metabolic syndrome, pre-diabetes and diabetes.

While correction of systemic hypercholesterolemia in vascular related disorders has been extensively studied, strategies to reduce local cholesterol accumulation at the plasma membrane and cellular level in target organs of obesity, metabolic syndrome, prediabetes and diabetes have not been studied.

Accumulation of cholesterol in patients with obesity, metabolic syndrome or diabetes has been described in several organs such as pancreas, muscle, liver, blood vessels, kidneys, although the functional consequences of accumulation of local cholesterol in these organs remains to be established.

In both clinical and experimental renal disease, for example, renal accumulation of cholesterol correlates with the development of glomerulosclerosis, and kidneys from diabetic rats are characterized by cholesterol accumulation. Excessive accumulation of cholesterol may be deleterious to cell function though several mechanisms including a modulation of cellular actin cytoskeleton, a modulation of the response of podocytes to several circulating factors (insulin, IGFs, VEGF, any growth factor, apolipoproteins, adipokines, endocrine hormones), a modulation of locally produced inflammatory cytokines, chemokines and their receptors, integrins, a modulation of the immune response (such as the one mediated through TLRs and co-stimulatory molecules as B7-1-CD80), or a modulation of pro- and anti-apoptotic cell death pathways.

Furthermore we have recently demonstrated an important role of a sphingolipid related enzymes (acid sphingomyelinase-like phosphodiesterase 3b, SMPDL3b) as modulators of podocyte function, which are kidney cells heavily affected in diabetes. Similarly, glycosphingolipids accumulate in the kidney of diabetic rats. However, no data are available yet showing a beneficial effect of plasma membrane or cellular cholesterol removal in proteinuric or other renal-related diseases such as diabetic kidney diseases.

Therefore, what is needed is an intervention method that can modulate the accumulation of plasma membrane and cellular cholesterol observed in disease. Such method may then be useful in a preventive and therapeutic strategy for treating, inhibiting or ameliorating such conditions as diabetes, prediabetes, metabolic syndrome, obesity, or symptoms thereof.

Cyclodextrins (CD) are cyclic oligosaccharides that contain 6 or more D-(+) glucopyranose units that are attached by α, β, or γ-(1,4) glucosidic bonds. It has been shown that cyclodextrins are able to form complexes with a variety of hydrophobic molecules due to their unique structure. Cyclodextrin derivatives are extensively used in research labs, for example to remove cholesterol from cultured cells and they are well known in the pharmaceutical industry for their ability to solubilize drugs.

Underivatized cyclodextrins are used throughout the food industry to make cholesterol-free products, such as fat-free butter, eggs and milk products. Hydroxypropyl-beta-cyclodextrin (HPßCD) is recognized as a GRAS (Generally Recognized As Safe) material for use in food products in Asian and European countries and is being considered for similar certification in the United States. Millions of people worldwide are exposed to small amounts of cyclodextrin compounds every day in food, cosmetics and household products. CD derivatives are commercially available from CTD Holdings Inc. (http://cyclodex.com/). Pharmacological studies have suggested that the cholesterol depleting capacities of CD derivatives is approximately 20 times superior to the cholesterol depleting capacities of statins.

In addition to this common exposure to cyclodextrins, the potential safety and efficacy for CD use in therapies has also been recognized. For example, in April 2009, the US Food and Drug Administration (FDA) approved an Investigational New Drug (IND) protocol that allowed twins with a rare brain-destroying cholesterol disease called Niemann Pick disorder to undergo weekly intravenous infusions of HPßCD into their bloodstreams. However, subsequent research discovered that Hydroxypropyl-beta-cyclodextrin does not cross from the bloodstream into the brain. And on Sep. 23, 2010, the FDA granted clearance of an IND application to introduce Trappsol® Cyclo™ (HPßCD) into the brains of six year old identical twin girls dying from Niemann Pick Type C (NPC).

A summary of the IND submission for this indication and route of administration is publicly available at the address (http://addiandcassi.com/wordpress/wp-content/uploads/2009/09/Hydroxy-Propyl-Beta-Cyclodextrin-HPBCD-Summary.pdf).

What has not been previously described are uses of CD and CD derivatives for reducing cellular cholesterol or lipids of obesity, metabolic syndrome, pre-diabetes and diabetes or any related complications.

Advantageously, it has now been discovered that cyclodextrin compounds do not act by affecting the cholesterol synthetic pathway (as do the statins) but primarily by increasing the efflux mechanisms leading to cholesterol accumulation.

This discovery allows for cyclodextrin compounds to be more broadly utilized for the prevention and the cure of obesity, metabolic syndrome, pre-diabetes and diabetes or any related complications. Moreover, cyclodextrin derivatives or any cellular cholesterol-lowering agent belonging to a class of compounds other than statins (such as chromium picolinate, liver X receptor agonists) can also be used in a method as described herein.

One novel strategy to modulate cellular cholesterol include the modulation of sphingolipid related enzymes such as SMPDL3B (sphingomyelin phosphodiesterase, acid-like 3B), which we have demonstrated to modulate cellular cholesterol content and cell function

SUMMARY OF THE INVENTION

This invention relates to the method of administering to a patient in need thereof, a compound, such as a cyclodextrin or a cyclodextrin derivative, to lower plasma membrane or cellular cholesterol/lipid for a time and at a dose sufficient to prevent, treat, cure, or reverse obesity, metabolic syndrome, pre-diabetes, diabetes, diabetic kidney disease or conditions or symptoms relating thereto.

Generally, the invention concerns a method for reducing lipid content in a cell or plasma membrane of a cell in a patient suffering from a condition selected from diabetes (type 1), diabetes (type 2), prediabetes, obesity, metabolic syndrome, diabetic nephropathy, diabetic kidney disease, diabetic neuropathy, diabetic retinopathy, diabetes related microvascular complication, diabetes related macrovascular complications, atherosclerosis, peripheral vascular disease, coronary artery diseases, congestive heart failure, cardiac hypertrophy, myocardial infarction, endothelial dysfunction and hypertension, stroke, cerebrovascular accident, myocardial infarction, heart attack, cardiovascular accidents, fatty liver, steatohepatitis, NASH, and insulin resistance, diabetic kidney disease, obesity, and metabolic syndrome, said method comprising administering to the patient an effective amount of a compound which reduces cellular lipid content.

More specifically, a method of the invention comprises inhibition of a cellular influx mechanism or increases a cellular efflux mechanism relating to cholesterol accumulation, including, modulation of a sphingolipid enzyme to reduce cellular cholesterol accumulation. The method can also include interference with a cellular cholesterol synthetic pathway.

Preferably, a useful compound of the subject method is a cyclodextrin or a derivative of a cyclodextrin. More preferably, the cyclodextrin or derivative thereof is hydroxypropyl beta cyclodextrin (HPβCD).

The subject invention further contemplates pharmaceutical compositions useful for treating, preventing or ameliorating a condition or symptom as described. Compositions according to the invention comprise, as an active pharmaceutical ingredient (API), at least one cyclodextrin as described herein and a vehicle pharmaceutically acceptable for injectable administration. Preferably, a composition of the invention comprises hydroxyporpyl β cyclodextrin (HPβCD) or an analog, derivative, isomer or salt thereof.

Compositions of the invention can comprise two or more active ingredients, wherein the active ingredients can be two or more retinoid compounds, or can include one or more retinoid compound in combination with a non-retinoid compound. The active ingredients can be administered sequentially or concomitantly.

A preferable application of the subject method comprises treating, inhibiting or preventing a condition such as obesity, metabolic syndrome, pre-diabetes, diabetes, diabetic kidney disease or conditions or symptoms relating thereto in a patient suffering from or predisposed to such condition.

The method comprises administering the effective amount of the compound, such as a cyclodextrin or derivative of a cyclodextrin, by a common route of administration, such as intramuscular, intraperitoneal, intravenous (systemic), subcutaneous, transdermal, oral, rectal, inhalation, topical, and intranasal. A preferred route of administration is subcutaneous.

Dosage ranges for administering a compound in accordance with a method of the subject invention comprise from about 2-20 mg/kg/day to about 4000 mg/kg three to five times per week (totaling up to about 20,000 mg·kg/week), and can be administered at least two times per week up to about three times per day.

Preferably, the method employs administering the compound as a single active ingredient, wherein more than one compound in the same class of compounds is considered a single ingredient. For example, administration of HPβCD plus a derivative of HPβCD, both being in the class of cyclodextrins, is considered a single active ingredient or single cyclodextrin for purposes of the subject invention. Typically, the compound is administered as a composition comprising the active ingredient and at least one pharmaceutically acceptable excipient or vehicle.

Alternatively, the method can employ the use of more than one active pharmaceutical ingredient, wherein the composition comprises two active ingredients, each from a different class of compounds where at least one of the compounds is a cyclodextrin. For example, the method can comprise administering a first active ingredient comprising one of more cyclodextrin or derivative thereof, and a second active ingredient which is not a cyclodextrin or derivative thereof, and preferably a pharmaceutically acceptable excipient or vehicle. For purposes of the subject invention, a pharmaceutically acceptable excipient can include a preservative.

The second active ingredient can be selected from an antidiabetic agent, a cholesterol biosynthesis inhibitor, a cholesterol absorption inhibitor, a bile acid sequestrant, niacin or niacin derivative, a fibrate, a cholesteryl ester transferase protein, and an acetyl-coenzyme A acetyltransferase inhibitor or a biologic. Alternatively, the second active ingredient can be selected from an immunosuppressive agent, insulin, sulphonylurea, gliptin, metformin, thiazolidinedione, insulin sensitizer, incretin analogue, DPP4 inhibitor, VEG-interfering agent, growth factor, antiinflammatory, vitamin D derivative, RAS system blocker, and aldosterone blocker.

The method of the invention further includes treating, inhibiting, preventing, or ameliorating a condition, or a symptom or secondary condition caused by accumulation of cholesterol in a cell or plasma membrane of a cell. These conditions are listed above and incorporated herein by reference. This embodiment of the invention can comprise administering to a patient suffering from the condition, or symptom or secondary condition, an effective amount of a compound which reduces cellular accumulation of cholesterol by affecting a cellular influx mechanism or a cellular efflux mechanism relating to cholesterol accumulation. The method can include modulation of a sphingolipid enzyme to reduce cellular cholesterol accumulation, and can further include effecting interference with a cellular cholesterol synthetic pathway.

In addition, the subject invention comprises a composition for treating, inhibiting, preventing, or ameliorating a symptom or related condition caused by, cellular accumulation of cholesterol, wherein the composition comprises an effective amount of at least one cyclodextrin or derivative of cyclodextrin, and a pharmaceutically acceptable excipient or vehicle.

The composition can further comprises a second active pharmaceutical ingredient which is not a cyclodextrin or a derivative of a cyclodextrin. The second active ingredient can be an antidiabetic agent, a cholesterol biosynthesis inhibitor, a cholesterol absorption inhibitor, a bile acid sequestrant, niacin or niacin derivative, a fibrate, a cholesteryl ester transferase protein, and an acetyl-coenzyme A acetyltransferase inhibitor or a biologic.

Alternatively, the second active ingredient can be an immunosuppressive agent, insulin, sulphonylurea, gliptin, metformin, thiazolidinedione, insulin sensitizer, incretin analogue, DPP4 inhibitor, VEG-interfering agent, growth factor, antinflammatory, vitamin D derivative, RAS system blocker, and aldosterone blocker.

In commercial use, the compound, composition and method of using the composition is useful in connection with a product or article of manufacture comprising the composition, as contained in a container, wherein the container is packaged with written instruction for using the compound or composition in accordance with a method for treating a condition caused by, or symptom resulting from, cellular accumulation of lipid, as described herein.

A preferred article of manufacture comprises a compound or composition of the invention, and written instruction indicating its use in treating cellular cholesterol accumulation, or a condition or symptom associated with cellular cholesterol accumulation.

BRIEF DESCRIPTION OF THE FIGURES

FIG. 1A-FIG. 1I show results of experiments illustrating CD improves diabetes in vivo, specifically, 1-Cholesterol was depleted by subcutaneous injection of hydroxypropyl-beta-cyclodextrin (CD) reverting diabetes and obesity in experimental animals and improving human islet cell function ex vivo.

FIG. 2A-FIG. 2I show results of experiments illustrating CD protects from Diabetic Kidney Disease in vivo, specifically, 2-Cholesterol was depleted by subcutaneous injection of Hydroxypropyl-beta-cyclodextrin (CD) and improves albuminuria, kidney weight and histological features of diabetic kidney disease.

FIG. 4A-FIG. 4J illustrate that 4-cholesterol accumulation occurs in podocytes exposed to the sera of patients with Diabetes and Diabetic Kidney Disease (DKD+), when compared to normal healthy controls and to patients with Diabetes without Kidney Disease (DKD−).

FIG. 5A-FIG. 5F show that CD protects podocytes from changes observed after exposure to DKD+ sera, specifically illustrating that cholesterol depletion with CD prevents several phenotypic changes, such as cell blebbing, cholesterol accumulation and cell apoptosis, observed in normal kidney cells (human podocytes) exposed to the sera of patients with diabetic kidney disease.

FIG. 6A-FIG. 6F show expression of sphingolipid related enzymes, e.g., SMPDL3b, are increased in diabetes in target organs such as the kidney and causes lipid dependent damage.

DETAILED DESCRIPTION OF THE INVENTION

It is known that elevated cholesterol levels, and in particular low-density lipoprotein (LDL) cholesterol, in the plasma play an important role in the development of microvascular and macrovascular complications of diabetes. Currently available treatments to lower cholesterol levels in patients, however, aim on lowering plasma LDL by blocking the synthesis of cholesterol in the liver (statins), by preventing reabsorption of cholesterol into the circulatory system (bile acid resins, cholesterol absorption inhibitors), or by increasing HDL cholesterol (fibrates, niacin derivatives, cholesteryl ester transfer protein [CETP]inhibitor). None of the currently used medications aims on lowering plasma membrane or cellular cholesterol, except for liver x receptor agonists (LXR), which have not yet been found to be safe in humans.

One embodiment of the invention relates to metabolic disorders which can be selected from a list comprising: diabetes (type 1 or type 2), prediabetes, obesity, metabolic syndrome, diabetic nephropathy, diabetic kidney disease, diabetic neuropathy, diabetic retinopathy, diabetes related microvascular complication, diabetes related macrovascular complications, atherosclerosis, peripheral vascular disease, coronary artery diseases, congestive heart failure, cardiac hypertrophy, myocardial infarction, endothelial dysfunction and hypertension, stroke, cerebrovascular accident, myocardial infarction, heart attack, cardiovascular accidents, fatty liver, steatohepatitis, NASH, insulin resistance.

In another embodiment of the invention, the drug used to prevent, treat, cure or reverse renal-related disorders is any drug that lowers the plasma membrane and cellular cholesterol content of the cell.

The drug can hereby be administered to an individual in a variety of ways. Routes of administration include, intramuscular, intraperitoneal, intravenous (systemic), subcutaneous (alone or in combination with drugs that facilitate administration of relatively large volume of subcutaneous drugs), transdermal, oral, rectal, inhaled, topical, and intranasal routes. The drug can be administered together with other biologically active agents or components as pharmaceutically acceptable carriers, diluents, excipients and vehicles.

A cyclodextrin described herein can be formulated into a pharmaceutical composition. In one aspect, a compound can be combined with at least one pharmaceutically-acceptable carrier to produce a pharmaceutical composition, prepared using techniques known in the art. In one aspect, a composition is prepared by admixing the compound with a pharmaceutically-acceptable carrier. Depending upon the components to be admixed, the components may or may not chemically or physically interact with one another.

Compositions provided herein may be formulated to include at least one cyclodextrin, together with one or more pharmaceutically acceptable carriers, including excipients, such as diluents, binders and the like, and can further include additives, such as stabilizing agents, preservatives, solubilizing agents, and buffers, as desired.

Pharmaceutical compositions may include carriers, thickeners, diluents, buffers, preservatives, surface active agents and the like, in addition to the active ingredient. Pharmaceutical compositions may also include more than one active ingredient, such as a retinoid compound according to the invention, and one or more antimicrobial agents, antiinflammatory agents, anesthetics, or the like. Pharmaceutically-acceptable carriers are known to those skilled in the art. These most typically would be standard carriers for administration to humans, including solutions such as sterile water, saline, and buffered solutions at physiological pH.

The pharmaceutical composition may be formulated for administration in a number of ways depending on whether local or systemic treatment is desired, or depending on the area to be treated. Administration can be topical, including ophthalmically, vaginally, rectally, intranasally, applied to the surface of the skin, or the like, as would be readily understood by persons of ordinary skill in the art.

In practical use, a provided compound of the present invention can be combined as the active ingredient in an admixture with a pharmaceutical carrier or vehicle according to conventional pharmaceutical compounding techniques. The carrier used can forms depend on the dosage form desired for administration, for example, oral, parenteral (including intravenous), urethral, vaginal, nasal, dermal, topical, transdermal, pulmonary, deep lung, inhalation, buccal, sublingual administration, or the like.

If in an aqueous solution, as preferred, a provided cyclodextrin composition may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, a suitable preservative may be employed, to prevent or limit bacteria and other microbial growth. One such preservative that may be employed is 0.05% benzalkonium chloride.

Preparations for administration include sterile aqueous or non-aqueous solutions, suspensions, and emulsions. Examples of aqueous or non-aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils.

Intravenous vehicles can be fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. It will be appreciated that the actual preferred amounts of active compound in a specified case will vary according to the specific compound being utilized, the particular compositions formulated, the mode of application, and the particular situs and mammal being treated.

In preparing the compositions for oral dosage form, typical pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

For solid administration formulations, any of a variety of thickening, filler, bulking and carrier additives may be employed, such as starches, sugars, fatty acids and the like. Formulation excipients may include polyvinylpyrrolidone, gelatin, hydroxy cellulose, acacia, polyethylene glycol, mannitol, sodium chloride and sodium citrate. For injection or other liquid administration formulations, water containing at least one or more buffering constituents is preferred, and stabilizing agents, preservatives and solubilizing agents may also be employed.

It is also contemplated that provided compounds of the present invention may be in a dried and particulate form. In certain embodiments, the particles are between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization.

For pharmaceutical formulations, it is also contemplated that any of a variety of measured-release, slow-release or time-release formulations and additives may be employed, so that the dosage may be formulated so as to effect delivery of a provided compound over a period of time, commonly referred to as controlled, delayed, extended, slow, or sustained, release formulations. For example, gelatin, sodium carboxymethylcellulose and/or other cellulosic excipients may be included to provide time-release or slower-release formulations, especially for administration by subcutaneous and intramuscular injection.

Provided cyclodextrins of the present invention may be therapeutically administered by means of an injection, typically a subcutaneous or intramuscular injection, such as in the gluteal or deltoid muscle, of a time release injectable formulation. In one embodiment, a provided compound of the present invention is formulated with a PEG, such as poly(ethylene glycol) 3350, and optionally one or more additional excipients and preservatives, including but not limited to excipients such as salts, polysorbate 80, sodium hydroxide or hydrochloric acid to adjust pH, and the like.

The formulation may be such that an application, administration, or injection is required on a daily, weekly, monthly or other periodic basis, depending on the concentration and amount of a provided compound, the biodegradation rate of a polymer used in the formulation, and other factors known to those of skill in the art.

In another embodiment, the drug used to prevent, treat, cure or reverse renal-related disorders is Cyclodextrin or any of its derivatives or analogs.

In another embodiment, Cyclodextrin is used to prevent, treat or reduce hyperglycemia (fasting or postprandial) in patients.

The present disclosure also relates to methods reducing the plasma membrane or cellular cholesterol content in any cells of any organ as a tool to prevent, treat, cure or reverse obesity, metabolic syndrome, pre-diabetes and diabetes related disorders.

In one embodiment, the plasma membrane or cellular cholesterol content is reduced in any cell of the body as a tool to prevent, treat, cure or reverse obesity, metabolic syndrome, pre-diabetes and diabetes related kidney disorders. A compound or composition of the invention can employ a cyclodextrin for treating, inhibiting, preventing, reducing, or reversing cholesterol accumulation in a cell or plasma membrane of a cell of a central or peripheral organ affected by diabetes or which is responsible for the development of diabetes.

In another embodiment, the plasma membrane or cellular cholesterol content is reduced in pancreatic beta cells to prevent, treat, cure or reverse impaired glucose stimulated insulin release, local or systemic inflammation and or the autoimmune attack to pancreatic islets.

In another embodiment, Cyclodextrin or its derivatives are used to at least partially deplete cells from plasma membrane cholesterol alone or in combination with other drugs currently used or being studied for the prevention and the treatment of diabetes such as immunosuppressive agents, insulin, sulphonylureas, gliptins, metofrmin, TZDs or any insulin sensitizers, incretin analogues and DPP4 inhibitors, agents interfering with VEGF and other growth factors, antinflammatory medications, vitamin D derivatives, blockers of the RAS system and of aldosterone.

In another embodiment, Hydroxypropyl Beta Cyclodextrin (HPβCD) is safe when administered to mice at a dose ranging from about 2 to about 20 mg/kg/day and can be administered in amounts up to about 4,000 mg/kg from three times to five times per week (totaling about 20,000 mg/kg/week).

In another embodiment, Hydroxypropyl Beta Cyclodextrin (HPβCD) is safe when administered subcutaneously at doses as high as 4000 mg/kg three times a week.

In another embodiment, Cyclodextrin, its derivatives, or any other plasma membrane or cellular cholesterol lowering drug is used in combination with a cholesterol biosynthesis inhibitor, such as a HMG-CoA reductase inhibitor. HMG-CoA reductase inhibitor drugs include drugs such as Simvastatin, Atorvastatin, Lovastatin, Rosuvastatin, Mevastatin, Pravastatin, Fluvastatin, Pitavastatin, Rosuvastatin, Cerivastatin, Rivastatin, Itavastatin, or ZD-4522.

In another embodiment, Cyclodextrin, its derivatives, or any other plasma membrane or cellular cholesterol lowering drug is used in combination with a cholesterol absorption inhibitor, such as a Ezetimibe, SCH-48461.

In another embodiment, Cyclodextrin, its derivatives, or any other plasma membrane or cellular cholesterol lowering drug is used in combination with bile acid sequestrants and resins (Colestipol, Colestilan, Colextran, Cholestyramine, Colesevelam).

In another embodiment, Cyclodextrin, its derivatives, or any other plasma membrane or cellular cholesterol lowering drug is used in combination with Niacin and Niacin derivatives such as Niceritrol, Nicofuranose, Niacin, Nicotinyl alcohol, Acipimox.

In another embodiment, Cyclodextrin, its derivatives, or any other plasma membrane or cellular cholesterol lowering drug is used in combination with fibrates such as Fenobrate, Simfibrate, Ronifibrate, Ciprofibrate, Clinofibrate, Clofibride, Etofibrate, Clofibrate, Bezafibrate, Aluminium clofibrate, Gemfibrozil.

In another embodiment, Cyclodextrin, its derivatives, or any other plasma membrane or cellular cholesterol lowering drug is used in combination with cholesteryl ester transfer protein (CETP) inhibitors such as Dalcetrapib, Torcetrapib, Anacetrapib.

In another embodiment, Cyclodextrin, its derivatives, or any other plasma membrane or cellular cholesterol lowering drug is used in combination with Acetyl-Coenzyme A acetyltransferase (ACAT) inhibitors (such as avasimibe) or microsomal triglyceride transport inhibitors.

These combination treatments may also be effective for the treatment or control of one or more obesity, metabolic syndrome, pre-diabetes and diabetes related disorders selected from the group consisting of atherosclerosis, insulin resistance, hyperlipidemia, hypertriglyceridemia, dyslipidemia, high LDL, and low HDL.

EXAMPLES

Experimental results showed increased cholesterol in association with down-regulation of ATP-binding cassette transporter ABCA1 occurs in normal human podocytes exposed to the sera of patients with type 1-diabetes and albuminuria (DKD+) when compared to diabetic patients with normoalbuminuria (DKD−) and similar duration of diabetes and lipid profile. Glomerular down-regulation of ABCA1 was confirmed in biopsies from patients with early DKD (n=70) when compared to normal living donors (n=32).

Induction of cholesterol efflux with cyclodextrin (CD) but not inhibition of cholesterol synthesis with simvastatin prevented podocyte injury observed in vitro after exposure to patient sera. Subcutaneous administration of CD to diabetic BTBR-ob/ob mice was safe and reduced albuminuria, mesangial expansion, kidney weight and cortical cholesterol content. This was followed by an improvement of fasting insulin, blood glucose, body weight, glucose tolerance in vivo and improved glucose stimulated insulin release in human islets in vitro.

Our data suggest that impaired reverse cholesterol transport characterizes clinical and experimental DKD and negatively influences podocyte function. Treatment with CD is safe and effective in preserving podocyte function in vitro and in vivo, in ameliorating human pancreatic beta cells ex vivo and in improving the metabolic control of diabetes in vivo We used a previously established cell-based assay in which differentiated human podocytes are exposed to 4% patient sera for 24 hours to identify new pathways and targets in DKD. Podocytes exposed to the sera of patients with DKD showed increased cholesterol accumulation in association with down-regulation of ABCA1 expression that was independent of circulating cholesterol. Excessive cholesterol deposition has indeed been described in glomeruli of rodent models of T1D and T2D and may contribute to DKD development and progression.

Research Design and Methods

Patient sera and kidney biopsies. Serum samples were obtained from ten healthy controls and twenty patients with T1 D from the Finnish Diabetic Nephropathy Study (Finn-Diane). T1 D was defined as onset of diabetes before 40 years of age and permanent insulin treatment initiated within 1 year of diagnosis. Urinary albumin excretion rate (AER) was defined as normal AER (<30 mg/24 h), microalbuminuria (30<300 mg/24 h), and macroalbuminuria (300 mg/24 h). Fasting glucose values were measured using a Hemocue device (Hemocue, Finland). Serum lipids were determined with a Konelab analyser (Thermo Scientific, Finland). Other biochemical analyses were performed in an accredited hospital laboratory (HUSLAB, Helsinki). For glomerular mRNA expression profiles, kidney biopsy specimens were procured from 70 Southwestern American Indians after obtaining informed consent. Human renal biopsies from pre-transplant, healthy living donors (n=32), membranous nephropathy (n=21) and focal segmental glomerulosclerosis (n=18) patients were obtained from the European Renal cDNA Bank.

Microarray analysis and PCR. For in vitro experiments, Illumina technology was utilized to study mRNA expression in human podocytes exposed to four independent pools of sera from 2-3 patients each (control, DKD− and DKD+). Glomerular mRNA expression profiles were performed with Affymetrix GeneChip arrays as described.

Human podocyte culture. Human podocytes were cultured and differentiated as previously described and serum starved in 0.2% FBS prior to experiments. When patient sera were utilized, starved cells were exposed to 4% patient sera for 24 hours. For insulin treatment experiments, 100 nmol insulin was added to the culture medium for 15 minutes after exposure to patient sera. For cyclodextrin or statin treatment experiments serum starved human podocytes were pretreated for 1 hour with 5 mM Methyl-beta-Cyclodextrin (CD, Sigma) or simvastatin (1 µM, Sigma).

Immunofluorescence staining. Cells cultured in chamber slides were fixed with 4% PFA for 30 minutes at 37° C. and permeabilized with 0.1% Triton X-100, followed by exposure to mouse-anti-phospho-Caveolin (pY14, BD Biosciences), anti-active-RhoA (New East Biosciences), or anti-vimentin (Sigma) antibodies. Fluorescence detection was performed using Alexa Fluor secondary antibodies (Invitrogen). For cholesterol determination, filipin (Sigma) staining was performed as described. F-actin was visualized by Rhodamine Phalloidin (Invitrogen). Two hundred consecutive cells per condition were studied. Slides were prepared with DAPI enriched mounting media (Vectashield) and analyzed by confocal microscopy.

Apoptosis analysis. Apoptosis was assessed using the Caspase-3/CPP32 Colorimetric Assay kit (Biovision) according to the manufacturer's description. Caspase 3 activity was normalized to cell number and expressed as fold change to controls.

Determination of cholesterol content. Esterified cholesterol was determined as difference between total and free cholesterol using an enzymatic assay and normalized to cell protein content. The cellular content of lipid droplets was determined using Oil red O (ORO). Cells were fixed and permeabilized as described above, washed in PBS and in 60% isopropanol, followed by incubation in ORO (0.5% ORO in isopropanol, 1:3 diluted) for 15 min at room temperature and counterstaining with hematoxylin for 1 min. The fraction of ORO positive cells over two hundred consecutive cells was calculated by bright field microscopy.

Western blotting and luminex. Cell lysate collection and Western blotting was performed as previously described. The following primary antibodies were used: rabbit-polyclonal-anti-MyD88 (Cell Signaling), rabbit-polyclonal-anti-phosphorylated (Y473) or anti-total-AKT (Cell Signaling), mouse-monoclonal-anti-rhoA (Santa Cruz), or mouse-monoclonal-anti-Gapdh (6C5, Calbiochem) antibody. Secondary Anti-mouse-IgG-HRP or and Anti-rabbit-IgG-HRP Conjugate (Promega) were used. Image acquisition was performed using the chemiluminescent imager SRX-101A (Konica Minolta medical imaging, USA) and band densitometry was analyzed using ImageJ software (NIH). Alternatively, phosphorylated/total AKT was quantified using luminex technology as previously reported.

Quantitative Real Time PCR (QRT-PCR). Podocyte RNA was extracted using the RNAeasy Mini Kit (Qiagen). Reverse transcription was performed using the high-capacity cDNA reverse transcriptase kit (Applied Biosystems) according to the manufacturer's protocols. QRT-PCR was performed in the StepOnePlus real-time PCR system (Applied Biosystems) using the PerfeCTa® SYBR® Green FastMix (Quanta Biosciences). Relative gene expression was determined as $2^\wedge$-$\Delta Ct$, with $\Delta Ct$ being the difference between the cycle threshold (Ct) value of the target gene and Gapdh. For semi-quantitative expression analysis, PCR was performed and analyzed by gel electrophoresis. Amplification product intensities were determined using ImageJ software (NIH), values were normalized and expressed as fold changes in gene expression over GAPDH. The following primers were used: hABCA1-F, AACAGTTTGTGGCCCTTTTG; hABCA1-R, AGTTCCAGGCTGGGGTACTT; hLDL-R-F, TCACTCCATCTCAAGCATCG; hLDL-R-R, GGTGGTCCTCTCACACCAGT; hHMG-CoA-R-F, GGCATTTGACAGCACTAGCA; hHMG-CoA-R-R, GCTGGAATGACAGCTTCACA; hGAPDH-F, GTCAGTGGTGGACCTGACCT; hGAPDH-R, Hs_ABCA1-SG QuantiTect-Primer-Assay (Qiagen); mAbca1-F, GGACATGCACAAGGTCCTGA; mAbca1-R, CAGAAAATCCTGGAGCTTCAAA.

BTBR ob/ob mice treatment and analysis. BTBR ob/ob mice were purchased from Jackson Laboratories. Mice were injected subcutaneously with 4,000 mg/kg CD or saline as reported previously, three times per week for 5 months. Urine was collected, and body weight and glycemia (One-Touch) were determined weekly. Six mice per group were analyzed. All animal procedures were approved by the Institutional Animal Care and Use Committee (IACUC). After isotonic saline perfusion, the right kidney was removed for cholesterol content determination and mRNA extraction. One left kidney pole was embedded in OCT, a second pole fixed in 4% PFA and paraffin-embedded for histological analysis. Blood samples were analyzed for CBC, lipid panel, AST, ALT, Alkaline Phosphatase, GGT, and BUN in the Comparative Laboratory Core Facility, University of Miami. Serum creatinine was determined by tandem mass spectrometry at the UAB-UCSD O'Brien Core Center, University of Alabama at Birmingham, using the methods previously described. The urine albumin content was measured by ELISA (Bethyl Laboratories). Urinary creatinine was assessed by an assay based on the Jaffe method (Stanbio). Values are expressed as µg albumin/mg creatinine. Fasting plasma insulin was determined by ELISA (Mercodia, SW). Intraperitoneal glucose tolerance tests (IP-GTT) were performed 4 months after treatment; after 5-hr fasting, blood glucose was recorded at baseline and up to 180 minutes after a glucose bolus (1.5 g/kg). For insulin sensitivity, glycemia was monitored at baseline and up to 150 minutes after intraperitoneal injection of 4 mU/g of short acting insulin. Human islets from four different isolations were pretreated with 0.5 mM CD for one hour and perfused as described before to determine insulin release in response to glucose and KCl.

Histology, assessment of mesangial expansion and glomerular surface area. Periodic acid-Shiff's (PAS) staining of 4 µm thick tissue sections was performed. Twenty glomeruli per section were analyzed for mesangial expansion by semiquantitative analysis (scale 0-4) performed by two blinded independent investigators. The glomerular surface was delineated in each encountered glomerulus and the mean surface area calculated as described.

SMPDL3b western blot was performed as we have previously reported. SMPDL3b overexpressing and knock down cell lines were also previously reported and are now utilized for the determination of cholesterol content and RhoA expression as described above.

Statistical analysis. Data are shown as mean and standard deviations. Four to 8 independent experiments were performed for in vitro studies. Six mice per group were used for in vivo experiments. Statistical analysis was performed with one-way ANOVA. When one-way ANOVA showed statistical significance, results were compared using t-test after Tukey's correction for multiple comparisons. Results were considered statistically significant at $p<0.05$.

Results

Clinical laboratory measurements and patient population. We studied 30 male subjects divided into three groups based on clinical characteristics at the time of collection of the sera samples. The study subjects included:

1) 10 patients with T1 D, normoalbuminuria and normal creatinine, defined as patients without diabetic kidney disease (DKD−), 2) 10 patients with T1 D, albuminuria and altered creatinine, defined as patients with diabetic kidney disease (DKD+), 3) 10 healthy controls (C).

The three groups were not significantly different for age, total cholesterol, HDL-, LDL-cholesterol and triglycerides. All patients were taking agents to block the renin-angiotensin-aldosterone system. Duration of diabetes, fasting plasma glucose and HbA1C were not significantly different among DKD+ and DKD− patients. The mean estimated glomerular filtration rate (eGFR) was 101 ml/min/1.73 m2 in DKD−, 97 ml/min/1.73 m2 in C and 43 ml/min/1.73 m2 in the DKD+ group. Sera collected seven years prior from five of the patients with DKD (mean eGFR 98 ml/min/1.73 m2) was utilized in selected experiments.

Podocytes exposed to DKD+ sera have a characteristic cDNA signature. RNA was extracted from differentiated podocytes cultured in the presence of patient sera as we previously reported. cDNA microarray analysis revealed that main pathways altered in DKD+ treated when compared to DKD− treated podocytes included genes involved in actin remodeling, insulin signaling, cytokine signaling (primarily through TLR4, TNF☐ and IL1☐), and apoptosis. We validated these findings at the protein level demonstrating by western blotting that in DKD+ treated podocytes, MyD88 expression was increased, the ability of insulin to phosphorylate AKT was impaired and the amount of cleaved caspase 3 was increased.

Normal human podocytes exposed to sera of patients with DKD exhibit cell blebbing. Podocytes exposed to the sera of patients with DKD experienced pronounced actin cytoskeleton remodeling with localized decoupling of the cytoskeleton from the plasma membrane (blebbing), which was evident in both the phalloidin staining (F-actin) and the brightfield images and which was very different from what we have reported in focal and segmental glomerulosclerosis. Quantitative analysis of cell blebbing (percentage of cells with blebs out of a total of 200 consecutive cells analyzed) revealed this phenotype in 80% of cells exposed to DKD+ sera, but in only 20% of cells exposed to DKD− sera and 5% in the controls. Cell blebbing was accompanied by the redistribution of active RhoA at the site of cell blebbing and by an increase in total RhoA. Cell blebbing was not a consequence of reduced GFR in the DKD+ group, as historical sera collected from five of the patients with T1 D and normal GFR that ultimately developed DKD caused the same degree of cell blebbing in cultured podocytes as the sera from the same patients collected on average 7-2 years later, when the patients had established DKD with macroalbuminuria and low GFR.

Impaired reverse cholesterol transport in podocytes exposed to DKD+ sera and in glomeruli from patients with early diabetes. As inflammation, insulin resistance, apoptosis and cytoskeleton remodeling are linked by the intracellular accumulation of lipids in the pathogenesis of non-alcoholic steatohepatitis (NASH syndrome), and accumulation of cholesterol has been described in the cortex of the kidneys of mice with DKD, we explored if podocytes cultured in the presence of sera of patients with DKD accumulate intracellular cholesterol. We were able to demonstrate an increased number of ORO and filipin positive cells in DKD− and DKD+ treated cells, more so in the DKD+ treated cells. Quantitative analysis of total, free and esterified cholesterol revealed significantly increased esterified cholesterol in DKD+ treated cells when compared to cells treated with sera from control subjects. This increase was likely due to impaired cholesterol efflux, as LDL-receptor and HMG-CoA reductase expression were unchanged, while ABCA1 mRNA expression was down-regulated in DKD+ treated podocytes. We then studied the mRNA expression of lipid related genes in glomeruli from additional 70 patients with T2D and early DKD when compared to 32 normal living donors, and demonstrated significant down-regulation of ABCA1 in DKD. Interestingly, down-regulation of ABCA1 mRNA expression was a feature of DKD only, as ABCA1 was not regulated in other proteinuric glomerular diseases such as membranous nephropathy (MN, n=21) and focal segmental glomerulosclerosis (FSGS, n=18).

Cyclodextrin protects podocytes in vitro. As the exposure of podocytes in culture to DKD+ sera caused accumulation of total cholesterol in association with decreased ABCA1 expression, a transporter responsible for cholesterol efflux, we went on to test the hypothesis that cyclodextrin would protect podocytes from the actin cytoskeleton remodeling and cell blebbing observed after exposure to the sera from patients with DKD. We were able to demonstrate that CD reduced the number of filipin-positive cells and preserved the localization of phosphorylated caveolin to focal adhesion sites. Quantitative cholesterol analysis showed that CD prevented the accumulation of total and esterified cholesterol in DKD+ treated podocytes. Furthermore, prevention of intracellular cholesterol accumulation with CD also prevented DKD+ induced apoptosis, insulin resistance and MyD88 expression. Blockade of HMG-CoA reductase with simvastatin in podocytes did not protect from DKD+ induced actin cytoskeleton remodeling.

Subcutaneous administration of CD protects BTBR ob/ob mice from the development of DKD. BTBR (black and tan, brachiuric) ob/ob (leptin deficient) mice have been described as a mouse model of progressive DKD. After establishing a dose and a mode of administration based on preliminary toxicology studies, we treated 4-week old BTBR mice with subcutaneous administration of three weekly injections of hydroxypropyl-β-cyclodextrin (CD, 4,000 mg/kg body weight) for five months. Although no changes in albumin excretion rates were observed up to 2 months after treatment initiation in homozygous mice, at 3 months a significant down-regulation of the albumin/creatinine ratios was observed in the morning spot urine samples ($p<0.001$) in CD treated when compared to untreated BTBR ob/ob mice. This decrease persisted until sacrifice (5 months after initiation of treatment. At sacrifice, CD treated mice showed a reduction of kidney weight. CD did not affect ABCA1 mRNA expression in the kidney cortex but resulted in a significant reduction of total cholesterol. Blood urea nitrogen (BUN) and creatinine were not significantly affected by CD treatment. However, CD treatment resulted in a reduction of mesangial expansion without affecting the glomerular surface area.

Figure 1A:
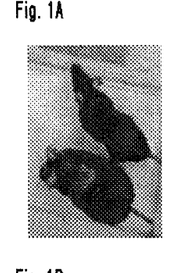
Figures 1B, 1C:
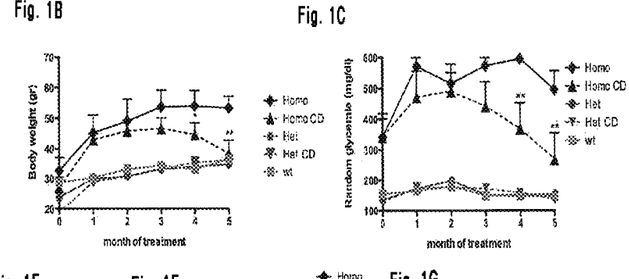
Figure 1D:
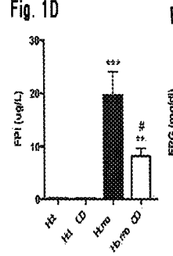
Figures 1E, 1F:
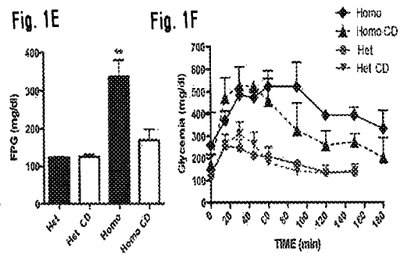
Figure 1G:
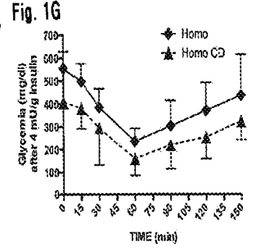
Figure 1H:
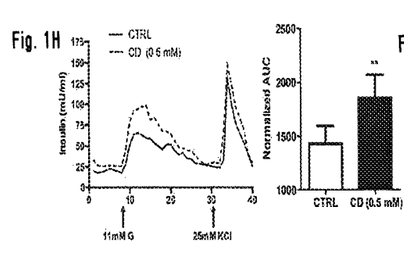
Figure 1I:
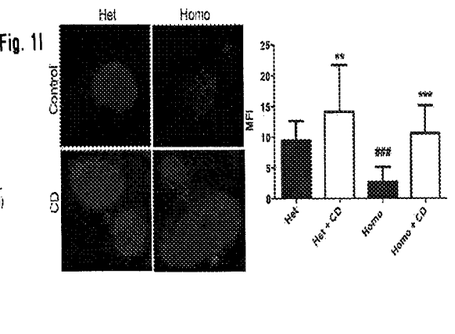
Figure 2A:
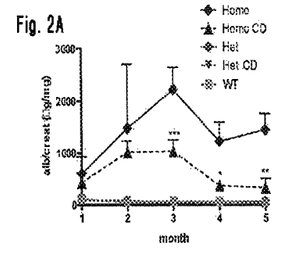
Figure 2B:
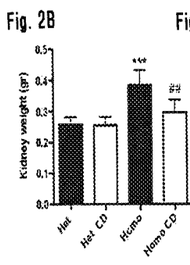
Figures 2C, 2D:
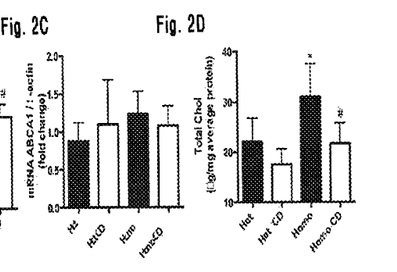
Figure 2E:
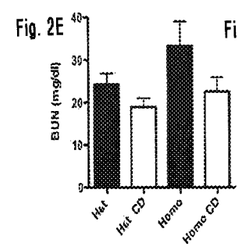
Figure 2F:
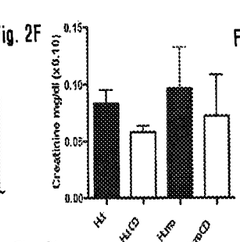
Figure 2G:
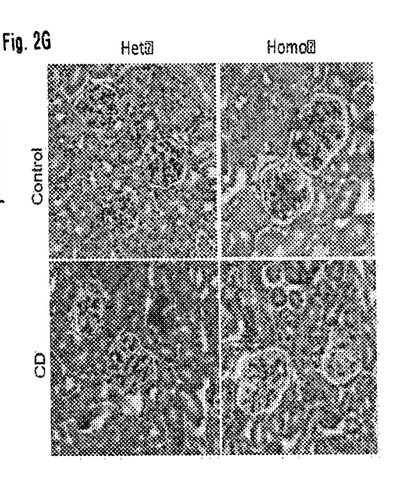
Figure 2H:
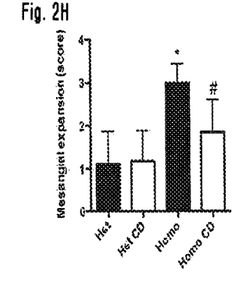
Figure 2I:
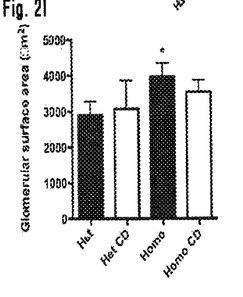
Figure 3:
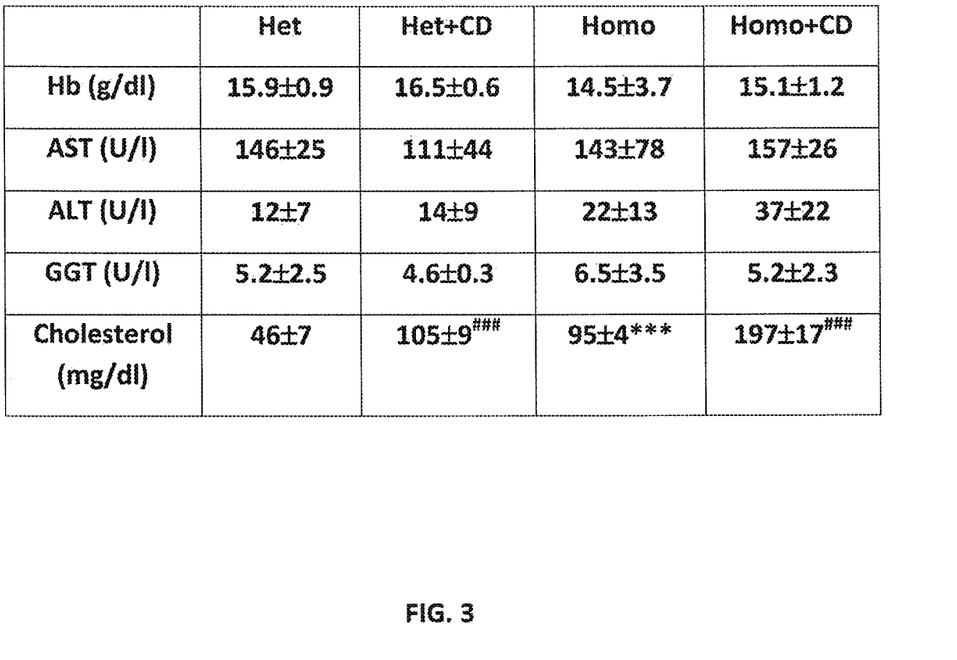
FIG. 3 is a Table summarizing the safety of CD in BTBR mice treated for five months (from the age of 4 weeks to the age of 24 weeks) with subcutaneous administration of three weekly injections of hydroxypropyl-β-cyclodextrin, specifically illustrating that 3-Cholesterol was depleted by subcutaneous injection of Hydroxypropyl-beta-cyclodextrin (CD) and was safe even when administered at very high doses of 4,000 mg/kg body weight.
Figure 4A:
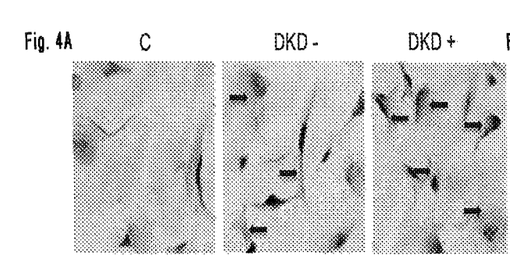
Figure 4B:
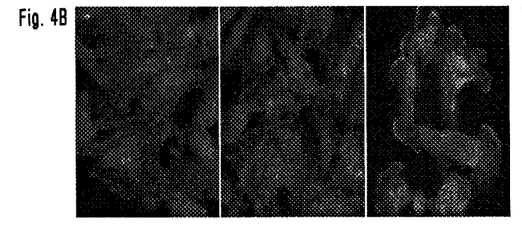
Figures 4C, 4D:
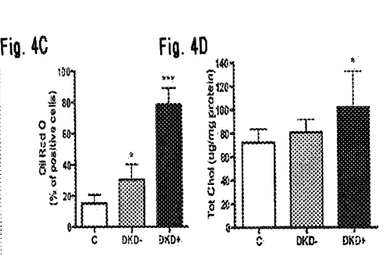
Figures 4E, 4F:
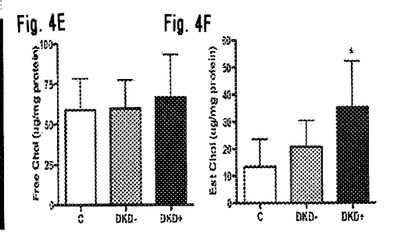
Figures 4G, 4H, 4I, 4J:
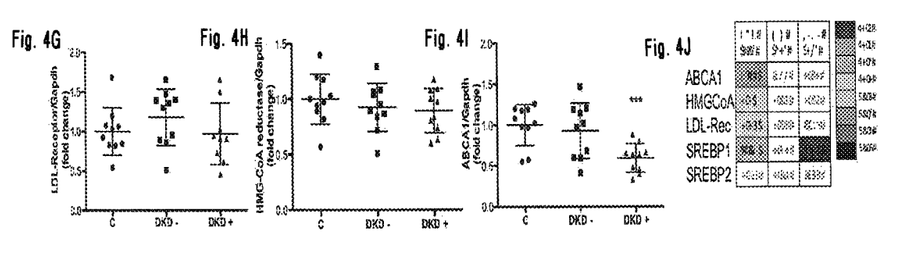
Figure 5A:
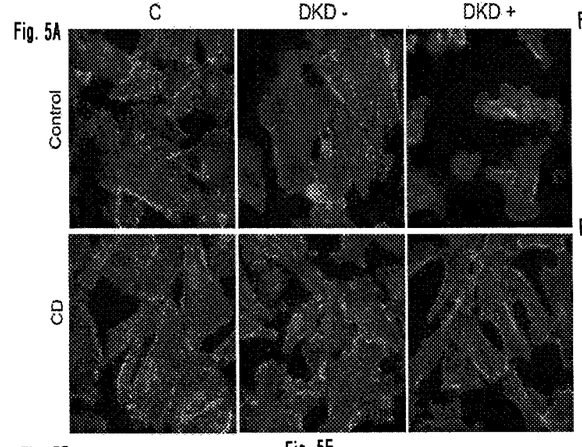
Figure 5B:
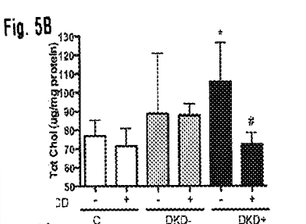
Figure 5C:
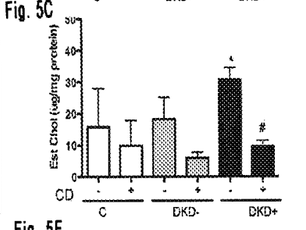
Figure 5D:
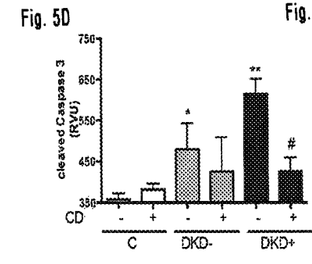
Figure 5E:
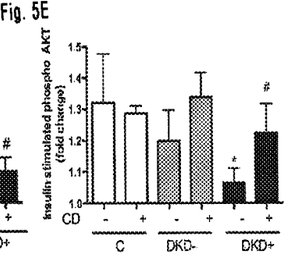
Figure 5F:
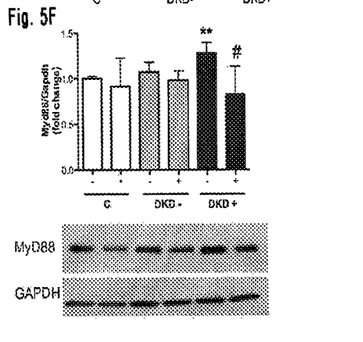

After four months of treatment, we also observed a reduction of body weight, which was accompanied by a concomitant improvement of random glycemia. Furthermore, sera collected at sacrifice demonstrated a significant improvement of fasting plasma insulin and fasting plasma glucose. IPGTT performed one week prior to sacrifice were improved in CD treated homozygous mice when compared to homozygous controls. As improvement was observed despite a similar insulin sensitivity test, we analyzed the effect of low dose CD on the function of four different preparations of human islet cells. A significant improvement in glucose stimulated insulin release was observed in CD treated human islets when compared to untreated human islets. To determine whether the beneficial effect of CD on islet cell function was associated with the modulation of ABCA1 expression in pancreatic islets, we performed immunofluorescence staining using a rabbit polyclonal ABCA1 antibody (gift from Dr. A. Mendez) and determined ABCA1 expression as mean fluorescence intensity per pancreata analyzed. Pancreata from homozygous BTBR ob/ob mice were characterized by significantly decreased ABCA1 expression when compared to heterozygous littermates ($p<0.001$) and CD treatment significantly increased ABCA1 expression in pancreata of homozygous BTBR ob/ob ($p<0.001$) and heterozygous BTBR ob/+ mice ($p<0.01$). As hemolytic anemia and liver toxicity have been described while using other cyclodextrin derivatives in rodents and humans, and because we administered high dose CD for a period of 5 months, we studied hemoglobin, aspartate aminotransferase (AST), alanine transaminase (ALT) and gamma-glutamyltransferase (GGT) at sacrifice. No abnormalities due to chronic CD administration were observed indicating that the chronic use of CD is not accompanied by adverse side effects (see Table).

Figures 6A, 6B, 6C:
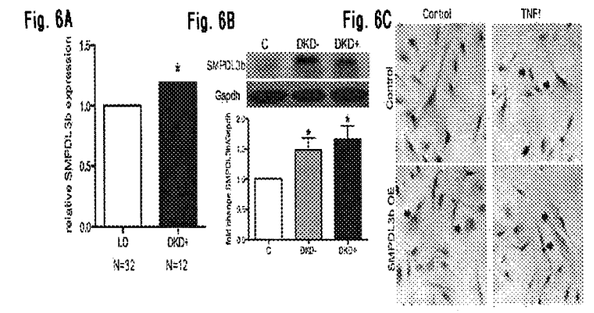
Figure 6D:
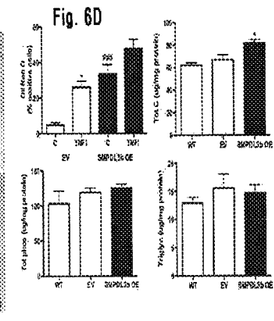
Figure 6E:
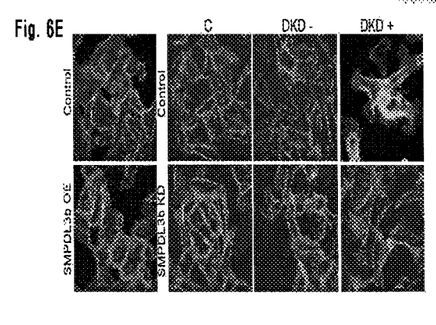
Figure 6F:
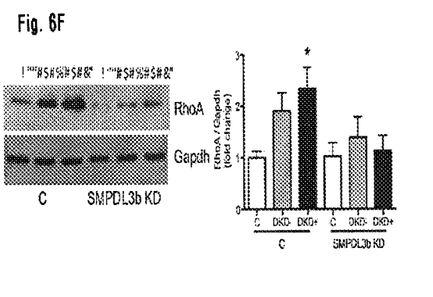

The efficacy and/or safety of the subject invention can be illustrated by reference to the figures appended hereto, the legends for which are provided below:

FIG. 1 shows a series of panels, (a) through (i) illustrating results of experiments or studies conducted which support that CD improves diabetes in vivo. Specifically referring to each of the panels of FIG. 1, (a,b) CD administered to homozygous and heterozygous BTBR ob/ob mice subcutaneously three times a week (n=6 per group) resulted in a significant reduction in body weight (mean±SD) starting at four month after the initiation of the treatment. *$p<0.05$, $p<0.01$. (c) CD administered to homozygous BTBR ob/ob mice resulted in a significant reduction in random glycemia (mean±SD) starting at four month after the initiation of the treatment. (d,e) Bar graph analysis (mean±SD) of fasting plasma insulin and glucose concentrations. Fasting plasma insulin ($p<0.01$; *$p<0.001$)(d) and fasting plasma glucose ($p<0.01$)(e) were significantly increased in homozygous mice when compared to heterozygous controls. The increase was prevented by CD treatment ($^{\#\#}p<0.01$). (f) IPGTT performed at 5 month after the initiation of the CD treatment showed improved glucose tolerance in CD treated BTBR ob/ob mice when compared to untreated BTBR ob/ob mice. (g) CD treatment did not affect the sensitivity to a single dose of short acting insulin (4 mU/g) in BTBR ob/ob mice. (h) Representative perifusion experiment and bar graph analysis of the area under the curve (AUC) demonstrating the effect of 0.5 mM CD on glucose stimulated insulin release in human pancreatic islets from four independent donors ($p<0.01$). (i) Immunofluorescence staining for ABCA1 reveals increased ABCA1 expression in pancreata of CD treated BTBR ob/ob mice when compared to untreated littermates (FIG. 6i, left). Bar graph analysis (FIG. 6i, right) showing that pancreata isolated from homozygous BTBR ob/ob mice are characterized by significantly decreased ABCA1 expression when compared to heterozygous littermates ($^{\#\#\#}p<0.001$). CD treatment significantly increased ABCA1 expression in pancreata of homozygous BTBR ob/ob (*$p<0.001$) and heterozygous BTBR ob/+ mice (**$p<0.01$).

FIG. 2 shows panels (a) through (i) supporting that CD protects from Diabetic Kidney Disease in vivo. (a) CD administered to homozygous and heterozygous BTBR ob/ob mice subcutaneously three times a week (n=6 per group) resulted in a reduction in albumin/creatinine ratios (mean±SD) starting at 3 months after the initiation of the treatment. *$p<0.05$, $p<0.01$, *$p<0.001$. (b) Kidney weight (mean±SD) was significantly increased in homozygous mice (***$p<0.001$), and such an increase was prevented by CD treatment ($^{\#\#}p<0.01$). (c) Bar graph analysis (mean±SD) of the effect of CD on ABCA1 mRNA expression in kidney cortexes of homozygous and heterozygous BTBR ob/ob mice. (d) Bar graph analysis (mean±SD) of the effect of CD on the total cholesterol content in kidney cortexes of homozygous and heterozygous BTBR ob/ob mice. (e, f) Bar graph analysis (mean±SD) showing that serum BUN and creatinine concentrations remain unchanged after CD treatment of the mice. Measurements were performed on serum obtained from the mice at sacrifice. (g) Representative PAS staining of kidney sections from homozygous and heterozygous BTBR ob/ob mice after five months of treatment with either CD or vehicle. (h, i) Bar graph analysis (mean±SD) of the scores for mesangial expansion (h) and of the glomerular surface area (i) on PAS stained kidney sections from homozygous and heterozygous BTBR ob/ob mice after five months of treatment with either CD or vehicle were assessed by two blinded, independent investigators. *$p<0.05$ when comparing DKD+ versus C. $^{\#}p<0.05$ when comparing CD treated versus untreated mice.

FIG. 3 is a table illustrating the safety of CD in 4-week old BTBR mice treated following subcutaneous administration of three weekly injections of hydroxypropyl-β-cyclodextrin (CD, 4,000 mg/kg body weight) for five months. As older and more toxic CD derivatives have been shown to cause anemia and liver toxicity, we tested the effect of long-term administration of high doses hydroxypropyl-β-cyclodextrin in diabetic and control mice.

In FIG. 4 (a) through (i), results are shown that cholesterol accumulation occurs in podocytes exposed to DKD+ sera (a) Representative Oil Red 0 staining of podocytes exposed to DKD+ sera when compared to C and DKD− sera. Black arrows point to spots of major lipid droplet accumulation. (b) Representative filipin staining (orange) and phosphorylated caveolin staining (green) of podocytes exposed to DKD+ sera when compared to C and DKD−. (c) Bar graph quantitative analysis (mean±SD) of Oil Red 0 positive cells in podocytes exposed to the pools of sera from 10 patients with DKD−, DKD+ or to pools of the sera from controls, demonstrating that exposure to both, DKD− and DKD+ sera, cause significant lipid droplet accumulation in cultured human podocytes. *$p<0.05$, ***$p<0.001$. (d, e, f) Bar graph analysis (mean±SD) of total cholesterol (Tot C), free cholesterol (Free C) and esterified cholesterol (Est C) as determined via enzymatic reaction in podocytes exposed to pools of DKD+ sera when compared to C and DKD−. *p<0.05. (g, h, i) Quantitative RT PCR analysis (mean±SD) of LDL receptor, HMG-CoA reductase and ABCA1 expression in podocytes exposed to individual patient sera. ***p<0.001. (j). Transcriptional analysis of glomerular gene expression of lipid related genes in 70 patients with early DKD, 21 patients with membranous nephropathy (MN) and 18 patients with focal segmental glomerulosclerosis (FSGS) when compared to 32 living donors. Numbers reflect fold change in disease when compared to living donors.

FIG. 5 panels (a) through (f) show that. CD protects podocytes from changes observed after exposure to DKD+ sera. (a) Representative phalloidin (red) and phosphorylated caveolin (green) confocal images of normal human podocytes exposed to DKD+ sera when compared to C and DKD− sera in the presence (CD) or absence (control) of CD. DAPI (blue) was used to identify nuclei (b, c) Bar graph analysis (mean±SD) of the effect of CD on total (B) and esterified cholesterol (C) in CD treated (+) versus untreated (−) podocytes exposed to DKD+ sera when compared to C and DKD− sera. *p<0.05 when comparing DKD+ versus C. #p<0.05 when comparing CD treated versus untreated podocytes in the same group. (d, e, f) Bar graph analysis (mean±SD) of cleaved Caspase 3, insulin stimulated AKT phosphorylation and MyD88 expression in CD treated (+) versus untreated (−) podocytes exposed to DKD+ sera when compared to C and DKD− sera. *p<0.05 and **p<0.01 when comparing DKD+ versus C. #p<0.05 when comparing CD treated versus untreated podocytes in the same group.

FIG. 6 panels (a) through (f) illustrates that expression of sphingolipid related enzymes, i.e. SMPDL3b, are increased in diabetes in target organs such as the kidney and causes lipid dependent damage. (a) Transcriptional analysis of glomerular gene expression of SMPDL3b in 12 patients with DKD when compared to 32 living donors. Numbers reflect fold change in disease when compared to living donors. *p<0.05 (b) Representative western blot and relative bar graph analysis for SMPDL3b protein expression in normal human podocytes cultured in the presence of sera from healthy controls (C) or age and sex matched diabetic patients with DKD (DKD+) or diabetic patients without DKD (but with the same diabetes duration and plasma lipid profile). p<0.05 (c, d) Representative Oil Red 0 staining and bar graph analysis of Oil Red O, Cholesterol, Trygliceride and Phospholipids in normal human podocytes and in podocytes overexpressing SMPDL3b (SMPDL3b OE) cultured in normal media (control) or in media supplemented with TNFα. *p<0.05 when comparing TNFα treated or SMPDL3b OE to controls. ###p, 0.001 when comparing Oil Red O staining in SMPDL3b OE versus empty vector (EV) control (□) Representative phalloidin staining demonstrating actin cytoskeleton remodeling in normal human podocytes exposed to DKD+ sera, a phenomenon that was prevented in cells where SMPDL3b was silenced (SMPDL3b KD). (f) Representative western blot and bar graph analysis demonstrating that SMPDL3b KD human podocytes are resistant to the increased RhoA expression observed after exposure to DKD+ sera. *p<0.05.

CONCLUSIONS

2-Hydroxypropyl-β-cyclodextrin (2-HPβCD), a strong cholesterol acceptor, is an effective way to sequester cholesterol and to protect any cell affected by diabetes, prediabetes, metabolic syndrome and obesity from cholesterol dependent damage in vivo and in vitro.

It is recognized that related inventions may be within the spirit of the disclosures herein. Also no omission in the current application is intended to limit the inventors to the current claims or disclosures. While certain preferred and alternative embodiments of the invention have been set forth for purposes of disclosing the invention, modifications to the disclosed embodiments may occur to those who are skilled in the art.

---

The invention claimed is:

1. A method for treating or reducing the progression of a proteinuric glomerular disease in a patient in need thereof, comprising administering to the patient an effective amount of hydroxypropyl beta cyclodextrin, or a derivative thereof, as an active agent, and a pharmaceutically acceptable excipient or vehicle, wherein the hydroxypropyl beta cyclodextrin is administered at a dose ranging from about 4-20,000 mg/kg/week.

2. The method of claim 1, wherein the hydroxypropyl beta cyclodextrin, or derivative thereof,
   (a) reduces cellular or plasma membrane lipid content, and/or
   (b) modulates a cellular mechanism to redistribute or reduce cellular cholesterol accumulation, said mechanism selected from the group consisting of inhibiting a cellular influx mechanism, increasing a cellular efflux mechanism, modulating ABCA1, and modulating a sphingolipid enzyme,
   whereby said proteinuric glomerular disease is treated, or the progression of the proteinuric glomerular disease is reduced.

3. The method of claim 1 wherein the compound further interferes with a cellular cholesterol synthetic pathway.

4. The method of claim 1 wherein the compound is hydroxypropyl beta cyclodextrin.

5. The method of claim 1, wherein the hydroxypropyl beta cyclodextrin, or derivative thereof, is administered by a route selected from the group consisting of intramuscular, intraperitoneal, intravenous (systemic), subcutaneous, transdermal, oral, rectal, inhalation, topical, and intranasal.

6. The method of claim 5 wherein the administration route is subcutaneous.

7. The method of claim 1, wherein the hydroxypropyl beta cyclodextrin, or derivative thereof, is administered at least one time per week up to about three times per day.

8. The method of claim 1, wherein the hydroxypropyl beta cyclodextrin, or derivative thereof, is administered as a composition consisting essentially of at least one hydroxypropyl beta cyclodextrin, or derivative thereof, as an active agent and at least one pharmaceutically acceptable excipient or vehicle.

9. The method of claim 1, wherein the hydroxypropyl beta cyclodextrin, or derivative thereof, is administered as a composition comprising hydroxypropyl beta cyclodextrin, or derivative thereof, and a second active ingredient which is not hydroxypropyl beta cyclodextrin or derivative thereof.

10. The method of claim 9, wherein the second active ingredient is selected from the group consisting of an antidiabetic agent, a cholesterol biosynthesis inhibitor, a cholesterol absorption inhibitor, a bile acid sequestrant, niacin or niacin derivative, a fibrate, a cholesteryl ester transferase protein, and an acetyl-coenzyme A acetyltransferase inhibitor, an ABCA1 modulator, a sphingolipid enzyme modulator, a recombinant ApoA1 or ApoA1 mimetic peptide, a HDL mimetic, a liver X receptor agonist, an immunosuppressive agent, insulin, sulphonylurea, gliptin, metformin, thiazolidinedione, insulin sensitizer, chromium picolinate, incretin analogue, DPP4 inhibitor, VEG-interfering agent, growth factor, antinflammatory, vitamin D derivative, RAS system blocker, an aldosterone blocker, and a biologic.

11. The method of claim 1, wherein the proteinuric glomerular disease is selected from diabetic nephropathy, diabetic kidney disease, obesity related glomerulopathy, membranous nephropathy and focal segmental glomerulosclerosis.

* * * * *